US012778793B2

(12) United States Patent
Arabin

(10) Patent No.: US 12,778,793 B2
(45) Date of Patent: Nov. 3, 2026

(54) VAGINAL PESSARY

(71) Applicant: Birgit Arabin, Berlin (DE)

(72) Inventor: Birgit Arabin, Berlin (DE)

( * ) Notice: Subject to any disclaimer, the term of this patent is extended or adjusted under 35 U.S.C. 154(b) by 93 days.

(21) Appl. No.: 18/739,611

(22) Filed: Jun. 11, 2024

(65) Prior Publication Data

US 2024/0407941 A1 Dec. 12, 2024

(30) Foreign Application Priority Data

Jun. 12, 2023 (DE) ..................... 10 2023 115 232.7
Nov. 24, 2023 (DE) ..................... 10 2023 132 833.6

(51) Int. Cl.
*A61F 6/08* (2006.01)
*A61F 2/00* (2006.01)

(52) U.S. Cl.
CPC ................ *A61F 6/08* (2013.01); *A61F 2/005* (2013.01)

(58) Field of Classification Search
CPC .... A61F 6/08; A61F 2/005; A61F 6/12; A61F 6/00; A61F 6/14; A61F 6/146; A61F 6/18; A61F 6/225; A61K 9/0036; A61K 9/0039
See application file for complete search history.

(56) References Cited

U.S. PATENT DOCUMENTS

| | | | |
|---|---|---|---|
| 186,469 | A | 1/1877 | Fowler |
| 1,790,801 | A | 2/1931 | Dickstein |
| 2,310,564 | A | 2/1943 | Younkins |
| 2,574,767 | A | 11/1951 | Stubbs |
| 4,139,006 | A | 2/1979 | Corey |
| D253,304 | S | 10/1979 | Nakao |
| 5,036,867 | A | 8/1991 | Biswas |
| 5,386,836 | A | 2/1995 | Biswas |
| 5,771,900 | A | 6/1998 | Austin |

(Continued)

FOREIGN PATENT DOCUMENTS

| | | | |
|---|---|---|---|
| DE | 10212832 | A1 | 10/2003 |
| DE | 102013018608 | A1 | 5/2015 |

(Continued)

OTHER PUBLICATIONS

Examination Report in corresponding German Application No. 10 2023 132 833.6, dated May 31, 2024, 11 pages, English translation.

(Continued)

*Primary Examiner* — Ophelia A Hawthorne
(74) *Attorney, Agent, or Firm* — Andrus Intellectual Property Law, LLP

(57) ABSTRACT

The present invention relates to a vaginal pessary having a circumferentially closed base body which has two side wall sections, a front (anterior) wall section and a rear (posterior) wall section and wherein a central opening of the base body in a cross-sectional view transverse to the height of the base (Continued)

body is bounded by a closed, inner oval contour line of the wall sections. According to the invention, it is provided that the inner contour line of the wall sections is delimited by a central opening deviating from the circular shape or by an essentially trapezoidal opening with rounded edges. The special feature of these designs is that there are one or more indentations in the walls, whereby the walls adhere better to the vaginal wall and thus provide a more secure hold.

19 Claims, 8 Drawing Sheets

(56) References Cited

U.S. PATENT DOCUMENTS

| | | | | |
|---|---|---|---|---|
| 6,413,206 | B2 | 7/2002 | Biswas | |
| D621,927 | S | 8/2010 | Dominguez | |
| 7,910,126 | B2 | 3/2011 | Ahmed | |
| 8,651,109 | B2 | 2/2014 | Ziv | |
| 9,248,285 | B2 | 2/2016 | Haessler | |
| 9,381,351 | B2 | 7/2016 | Haessler | |
| 10,441,402 | B2 | 10/2019 | Zeltwanger | |
| D945,145 | S | 3/2022 | Hilsabeck | |
| D1,034,987 | S | 7/2024 | Sui | |
| D1,071,181 | S | 4/2025 | Price | |
| 2010/0305395 | A1* | 12/2010 | Spitz | A61F 2/005 600/30 |
| 2024/0407941 | A1 | 12/2024 | Arabin | |

FOREIGN PATENT DOCUMENTS

| | | | |
|---|---|---|---|
| EM | 015024369-0001 | | 6/2023 |
| EM | 015024369-0002 | | 6/2023 |
| EM | 015024369-0003 | | 6/2023 |
| GB | 670349 | A | 4/1952 |

OTHER PUBLICATIONS

Harvey et al., “Guideline No. 411: Vaginal Pessary Use,” J Obstet Gynaecol Can. 2021;43(2):255-266, 13 pages.

Tunn et al, “Interdisciplinary S2k Guideline: Sonography in Urogynecology: Short Version—AWMF Registry No. 015/055,” Geburtshilfe und Frauenheilkunde, 2014, 74:1093-1098.

Haute Autorite De Sante, “Prolapsus genital de la femme - des solutions pour le traiter,” 2022, https://www.has-sante.fr/upload/docs/application/pdf/2022-04/reco443_fiche_patient_principale_prolapsus_cd_2022_04_28_v0.pdf.

National Institute for Health and Care Excellence, “Urinary incontinence and pelvic organ prolapse in women: management”, NICE Guideline, Jun. 24, 2019, www.nice.org.uk/guidance/ng123.

Lone et al., “One-year prospective comparison of vaginal pessaries and surgery for pelvic organ prolapse using the validated ICIQ-VS and ICIQ-UI (SF) questionnaires,” Int Urogynecol J., 2015, 26:1305-1312.

Dietz et al., “Levator avulsion and vaginal parity: do subsequent vaginal births matter?”, Int Urogynecol J., 2020, 31:2311-2315.

Hilde et al., “Postpartum pelvic floor muscle training, levator ani avulsion and levator hiatus area: a randomized trial,” Int Urogynecol J, 2022, 34:413-423.

Examination Report in corresponding German Application No. 10 2023 132 833.6, dated May 31, 2024, 11 pages.

* cited by examiner

| Photo | Modell-Nummer | Höhe vorn | Höhe hinten | Maximale Länge | Maximale Weite | Zugkraft [illegible] | Beschreibung |
|---|---|---|---|---|---|---|---|
|  | 1.0 | 13mm | 28mm | 70mm | 53 mm | 4/5/6 N<br>3/2/3 N | Trapezoid ohne Saugnapf |
|  | 2.0 | 13mm | 28mm | 70mm | 53mm | 18/20/19N<br>15/16/19N | Trapezoid mit 5 Saugnäpfen |
|  | 3.0 | 10mm | 30mm | 71mm | 66mm | 17/17/18N<br>17/16/18N | Ovale Form mit 3 Saugnäpfen und Einkerbung für Urethra |
|  | 4.0<br>92% | 10mm<br>8mm | 30mm<br>28mm | 72mm<br>66mm | 66mm<br>61mm | 19/19/19N<br>17/15/19N | Ovale Form mit 3 geschlossenen Saugnäpfen<br>Reduziert auf 82% in Volumen. |
|  | 4.1<br>92% | 10mm<br>9mm | 30mm<br>28mm | 72mm<br>66mm | 66mm<br>61mm | 7/8/9 N<br>7/7/9 N | Ovale Form mit 3 offenen Saugnäpfen<br>Reduziert auf 92% in Volumen. |
|  | 4.2<br>82% | 10mm<br>9mm | 30mm<br>28mm | 72mm<br>66mm | 68mm<br>62.5mm | 5/6/5 N<br>3/3/5 N | Ovale Form - Basis<br>Reduziert auf 82% in Volumen. |
| 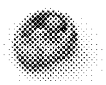 | 5.0 | 23 mm | 30 mm | 75mm | 66 mm | 14/16/15 N<br>14/12/12 N | Ovale Form mit 3 geschlossenem Saugnäpfen und Verstärkung für Urethra |
| 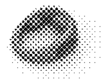 | 6.0 | 10mm | 30mm | 72mm | 66mm | 11/12/11 N<br>10/12/11 N | Ovale Form mit 3 flachen Saugnäpfen, hintere Vertiefung flach gerade geschlossen. |
| 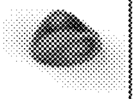 | 7.0 | 11mm | 11mm | 75mm | 69mm | 18/18/18N<br>17/18/19N | Ovale Form mit 2 Saugnäpfen, hinten niedrig. |
| 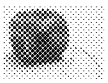 | Größe 3 | | | | | 4/9/11 N<br>4/5/5 N | Würfel 3 |
|  | 60 mm | | | | | 3/3/3 N<br>3/3/3 N | Ring 60mm |
| 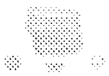 | | | | | | 3/3/3 N<br>6/5/5 N | Restifem |

Fig. 17

VAGINAL PESSARY

CROSS-REFERENCE TO RELATED APPLICATIONS

The present application claims priority to German Patent Application No. 10 2023 115 232.7, filed Jun. 12, 2023, and to German Patent Application No. 10 2023 132 833.6, filed Nov. 24, 2023, both of which are hereby incorporated by reference herein in their entireties.

FIELD

The present invention relates to a vaginal pessary with a circumferentially closed base body, wherein the base body has two (lateral) side wall sections, a front (anterior) wall section and a rear (posterior) wall section and wherein a central opening of the base body is bounded by a closed, inner contour line of the wall sections. In particular, the side wall sections together with the anterior wall section and the posterior wall section form a circumferential, i.e. self-contained, side wall of the pessary.

BACKGROUND

Vaginal pessaries of the type in question are used to treat gynecological conditions associated with a weakening of the uterine supporting apparatus or the internal organs adjacent to the vaginal area. The clinical picture affects around a third of all women and, depending on their constitution, occurs after pregnancies and births due to the associated stress. This results in gaps in care and high costs. Pessaries are therefore a minimally invasive, cost-effective alternative to high-risk surgery. They are now even recommended as the first choice before surgery in most countries (1-4).

Randomized studies have shown that urogynecological pessaries can treat prolapse symptoms just as well as surgery and can contribute to high patient satisfaction (5).

The previous models were mainly used to treat older patients suffering from prolapse and/or incontinence as a result of pregnancy and childbirth.

In obstetrics, other specific pessaries are used to prevent premature birth in singleton and multiple pregnancies. These are pessaries that are placed around the cervix, move the uterus sacralwards and reduce the pressure on the lower uterine segment. These are not discussed here.

The treatment of urogynaecological complaints (prolapse and/or incontinence) with vaginal pessaries is usually carried out with ring-shaped models such as ring, urethral or sieve-shell pessaries as well as with cube pessaries, which fit snugly against the vaginal wall thanks to their concave wall structures. In general, reliable fixation of the position of the pessaries inside the vagina is of great importance in order to provide adequate support for prolapse of internal organs or the urethra.

Previously used ring-shaped pessaries depend on the pelvic floor still being stable enough to support the pessary. They have the disadvantage that the vagina is not circular but rather oval and the side walls of the vagina are further dilated by the pessary, which can have an unfavorable effect on the clinical picture.

The fixation of a previously used cube pessary is based on the concave side walls, the surface of which lies against the mucous membrane and can thus fix the pessary in place. However, as these pessaries fill the entire space of the vagina, they have to be removed every evening and reinserted during the day. This is inconvenient for many patients.

In addition, the cubes inevitably have a thread for handling, which can also bother patients in the long term. In this respect, the vaginal pessaries known from practice and the state of the art could be improved. In addition, the fixation of the ring-shaped pessaries at the expense of dilation and that of the cube pessaries at the expense of a discharge that may be impeded (e.g. during menstruation) are limited in their therapeutic treatment options.

More recent ultrasound examinations using the 3D method have also described the causes of prolapse complaints more specifically: There is often a tearing of the pelvic floor muscle "levator ani" from the pelvic wall (6). In this case, pelvic floor therapy no longer helps (7).

This new development was adapted to the findings described above. The raised side walls exert a kind of "massage function" on the lateral vaginal walls and lead to contractions of even torn muscle fibers in ultrasound.

SUMMARY

It is therefore an object of the present invention to provide a prototype of a vaginal pessary which permits reliable treatment without side effects in the context of the prevention and treatment of prolapse of internal organs and/or stress incontinence.

The above object is solved by a vaginal pessary with the features of the independent claims. Advantageous further developments are the subject of the dependent claims.

In the vaginal pessary according to the invention, it is provided that the inner contour line of the wall sections delimits an essentially egg-shaped central opening that deviates from the circular shape. This corresponds more closely to the actual anatomy and is intended to reduce the dilation of the lateral vaginal walls. The concave inwardly turned surfaces of the side walls are not only intended to improve the holding function of the pessary, but also to bring the lateral walls together, as the egg-shaped contour is optimally adapted to the anatomical conditions in the vaginal area when inserted and lies against the surrounding tissue structure without lateral stretching. Due to the nature of the outer walls, the vaginal pessary according to the invention assumes a reliable or resistant support function. Furthermore, the vaginal pessary according to the invention also has a high resistance to collapse or radially inward deformation, which continues to allow an efficient support function, since a sufficiently high radial outer seal is always ensured. In contrast to the cube pessary, it also allows fluorine or blood to drain away.

The term "egg-shaped" in the sense of the invention refers to the geometry of an inner contour line of a circumferential side wall of the pessary according to the invention, which delimits the central opening of the pessary, with reference to a plan view of the pessary.

Preferably, the opening has rounded corners. The opening can preferably have a pointed end in the area of an anterior wall section of the pessary in the inserted state of the pessary and a blunt end in the area of a posterior wall section.

The term "egg-shaped" in the sense of the invention is to be understood broadly.

The term "egg-shaped" or "oval" in the sense of the invention refers to a flat, rounded, convex figure or contour line of the central opening of the pessary according to the invention in a plane or in the plan view of the pessary, which resembles the profile of a bird's egg in the broadest sense. According to the invention, however, it does not comprise a circular shape, but possibly an ellipse as a special case.

An egg-shaped or oval, non-circular central opening within the meaning of the invention has in particular the following properties: The contour line of the center opening has in particular no loops or loops and/or the oriented curvature of the contour line has in particular no change of sign, i.e. depending on the sense of passage, the oriented curvature for each point of the contour line is either non-negative or non-positive, which means that it has no turns or indentations. The contour line can only be traversed in a pure left-hand or right-hand curve.

The curvature of the contour line of the central opening of the pessary according to the invention cannot disappear in any section.

However, it is preferable that the contour line of the central opening is also composed of arcs, in particular circular arcs, and at least one essentially straight contour line section or an arc-shaped contour line section with very little curvature.

Particularly preferably, the contour line is composed of a front, convex contour line section and a rear, also convex or preferably essentially straight contour line section. Preferably, the front, convex contour line section is more curved or more pointed than the rear, convex contour line section, which can then be described as “blunt”.

Particularly preferably, the contour line can have a rear, straight contour line section that is connected to the front, convex contour line section via two lateral convex contour line sections. The front, convex contour line section can be more curved than the two lateral contour line sections. The contour line is rounded, particularly at the transitions between the contour line sections.

The contour line of the central opening can have an axis of symmetry. However, this is not absolutely necessary. An egg-shaped inner contour line of the central opening of the pessary does not necessarily require a symmetrical design or a corresponding axis of symmetry. Asymmetrically formed contour lines are also covered by the teaching according to the invention if this improves the treatment. Nevertheless, a symmetrical, egg-shaped design of the inner contour line is preferred in order to be able to adapt to the anatomical conditions in a particularly reliable sealing manner when in use. A symmetrical design of the inner contour line has also proven to be advantageous for handling reasons in routine production.

In other words, the egg-shaped inner contour line, particularly in contrast to a circular contour line, is better adapted to the anatomy of the vagina. This improves the insertion and wearing comfort of the inserted vaginal pessary.

A trapezoidal inner contour line, preferably with rounded corners, can also be described as an egg-shaped contour line according to the invention.

Particularly preferably, the inner contour line has an at least substantially egg-shaped course with a substantially pointed end on the side of the front (anterior) wall section and with a substantially blunt end on the side of the rear (posterior) wall section. In this respect, the egg-shape forms a preferred embodiment of the generally oval-shaped opening of the vaginal pessary according to the invention.

The elliptical shape represents a preferred design of the opening, which is limited by the inner contour line. The elliptical shape is mathematically defined and in particular in the form of a conical section.

In particular, it is therefore preferable for the front (anterior) wall section to have a smaller extension in the direction of contact than the rear (posterior) wall section. This results in the contour line being more pointed at the front end and more blunt at the rear end. This enables particularly precise and reliable adaptation to the anatomical conditions when the vaginal pessary is inserted. However, if the clinical picture is predominantly characterized by an anterior defect, the pessary can also be inserted with the other side facing forward.

According to a particularly preferred embodiment of the present invention, the front (anterior) wall section is convexly curved and/or the rear (posterior) wall section of the pessary according to the invention is essentially convexly curved or essentially straight. This allows a particularly gentle and at the same time reliable connection of the vaginal pessary.

Preferably, it is also provided that the front (anterior) wall section and/or the rear (posterior) wall section is or are substantially differently convexly curved in a plan view of the opening. The anterior wall section is preferably more curved than the posterior wall section in order to realize a more pointed or shorter design of the anterior wall section compared to the posterior blunt or longer wall section.

According to a preferred embodiment, the inner contour line of the central opening is mirror-symmetrical to a central longitudinal axis and/or central transverse axis of the base body. The mirror symmetry can relate to a single central axis, for example to a central longitudinal axis in the case of an egg-shaped or trapezoidal contour line. However, it is also possible for the contour line to be mirror-symmetrical to the central longitudinal axis and to a central transverse axis, for example if the inner contour line or the opening is elliptical.

Particularly preferably, the inner contour line has a continuous convex course along the central opening, which is more curved in the region of the front (anterior) wall section than in the region of the rear (posterior) wall section. In the area of the side wall sections, the inner contour line has the same curvature, whereas the inner contour line has a different curvature at the posterior and anterior wall sections.

According to a preferred embodiment, it is provided that the thickness of the wall sections, preferably the side wall sections, decreases starting from a proximal outer side of the base body towards a distal outer side of the base body. In other words, the wall thickness relative to the insertion state of the pessary in the body increases towards the center of the body. Alternatively or additionally, the wall sections, preferably the side wall sections, are tapered and/or tapered towards the distal outer side of the base body.

For example, the wall sections, in particular the side wall sections, are teardrop-shaped and/or egg-shaped in a cross-section perpendicular to the opening or the base body.

The side wall sections are particularly flap-shaped. This also facilitates insertion into the vaginal area as a side effect.

Alternatively, the aforementioned object is also solved by the wall sections of the vaginal pessary according to the invention defining an essentially trapezoidal opening. This also allows corresponding advantages to be realized.

An inner contour line to form a trapezoidal opening is also to be understood broadly and does not necessarily require straight wall sections to form the inner contour line. For example, curved or convex wall sections, particularly in the area of the side wall sections, can also form a trapezoidal inner contour line.

In a vaginal pessary according to an aspect that can also be realized independently, the aforementioned object is solved in accordance with the invention in that the base body has a height of the circumferential side wall that preferably changes continuously in the circumferential direction, whereby, preferably, a smaller height can be achieved at the anterior wall section and/or a greater height can be achieved at the posterior wall section. The height at the anterior wall section and the height at the posterior wall section can also be essentially the same. The side sections preferably have the greatest height, further preferably in a central region of the side wall sections, wherein the height decreases from a maximum height to the height at the anterior wall section and/or the height at the posterior wall section. The term "height" in the sense of the invention describes the extent or the expansion of the wall sections between a distal outer surface and a proximal outer surface of the wall sections.

According to the invention, the change in height in the circumferential direction of the base body is preferably steady and/or continuous. A minimum height can be achieved at the anterior wall section and a maximum height at the posterior wall section. However, it is also possible for the maximum height to be reached at one side wall section, in particular with the maximum height being reached at both opposite side wall sections.

The changing height in the circumferential direction of the base body is associated with improved stability of the vaginal pessary with adjacent tissue sections. The changing height in the circumferential direction enables flexible adaptation to the anatomical conditions of the vagina, whereby reliable contact of the vaginal pessary in the circumferential direction with the adjacent tissue sections is always guaranteed.

Particularly preferably, the same minimum height is achieved on the anterior wall section and on the posterior wall section, especially where the maximum height is achieved on both side wall sections.

The proximal outer surfaces of the side wall sections, the front wall section and the rear wall section of the pessary preferably lie in one plane. On the distal outer side of the base body, the base body then has a height that changes in the circumferential direction.

According to a further aspect of the present invention, which can also be realized independently, it is provided in a vaginal pessary of the type mentioned at the beginning for solving the object in question that the base body, preferably on at least one side wall section, has at least one pocket-like deepening opened on the outside of the base body in order to form a better adhesion for adjacent tissue in the inserted state or in the inserted state of the vaginal pessary. The special feature of this embodiment is that one or more indentations or pocket-like deepenings are located in both side wall sections, in particular opposite each other in the side wall sections, whereby the walls adhere better to the vaginal wall and thus ensure a secure hold.

An essential feature of the present invention according to this aspect are the side walls, which are essentially convexly curved or arched inwards in the cross-sectional view. This allows a particularly gentle and at the same time reliable attachment of the vaginal pessary to the vaginal mucosa, as a partial vacuum effect is created. As a result, the pessary holds approx. 5 times better than a conventional ring pessary when pulled outwards during verification on the pig model (average test with closed indentations 18 Newtons compared to 3 Newtons of pulling force required for removal, see FIG. 17). FIG. 17 shows tensile measurements on the porcine vagina model, in which some models of the new development were compared with conventional models in order to detach them from the vagina. The tensile force was given in Newtons (N).

The aspect in question of the at least one pocket-like deepening in an associated wall section of the pessary has proved to be particularly advantageous with regard to the first aspect, according to which the inner contour line of the wall sections defines an opening which is essentially egg-shaped and deviates from the circular shape. While a pessary with an egg-shaped inner contour line adapts better to the anatomy inside the vagina, the at least one indentation or pocket-shaped deepening ensures that a reliable connection of the vaginal pessary to the vaginal mucosa is guaranteed despite the improved adaptability. In this respect, the anatomically adaptable egg-shaped design of the vaginal pessary is complemented in an appropriate manner by the indentation or pocket-shaped deepening. As a result, the two positive effects of the two aspects in question, namely the egg-shaped design on the one hand and the pocket-shaped deepening on the other, complement each other in a mutually reinforcing or synergistic manner, whereby a reliable fixation of the vaginal pessary at the place of use or in the state of use is made possible at the same time as a comfortable or pleasant wearing sensation.

Particularly preferably, the geometry of the pessary according to the invention is similar to a ring pessary with a non-circular cross-section, wherein, preferably, the side wall sections have a greater height compared to the posterior and anterior wall sections and/or are tab-like and/or taper distally, so that the pessary can be gripped and held at the side wall sections during insertion. The posterior and anterior wall sections can have an essentially circular cross-section. Further preferably, at least one pocket-like deepening is then provided in the central region of the respective side wall section, in which the side wall section reaches a maximum height, the insertion of the deepening being facilitated by the distally tapering wall thickness of the side wall section.

The pocket-shaped deepening or indentation in question thus functions as a receiving pocket and/or suction cup, whereby a negative pressure is generated during insertion within the pocket-shaped deepening or indentation in the state of contact with the adjacent tissue, accompanied by a particularly reliable and/or resistant fixation of the vaginal pessary at the insertion site.

The deepening can preferably be closed on the inside of the base body and then forms a pocket in the wall section of the base body that is closed on the inside and open on the outside of the pessary. Preferably, all deepenings can be closed. In the case of several deepenings, at least one deepening can also be closed and at least one can be open on the inside of the base body, whereby body fluids can be drained via an open deepening. However, it is also possible to design several deepenings on the inside of the base body to be open, with the proviso that at least one deepening is closed, in particular to ensure the suction effect.

Preferably, the deepening is directed radially inwards, whereby the deepening on the inside(s) of the base body is formed by a thin-walled wall section which is protruded inwards in relation to the wall sections of the base body adjacent to the deepening. The protrusion enables deformability and is intended to increase or generate the suction effect within the pocket-shaped deepening in the inserted state. The formation of a pocket-like deepening can lead to a merely negligible reduction in the rigidity of the vaginal pessary according to the invention compared to a geometrically identical vaginal pessary without a pocket-like deepening.

Particularly preferably, the formation of a pocket-like or pocket-shaped deepening leads to a merely negligible reduction in the rigidity of the vaginal pessary according to the invention compared to a conventional ring pessary as a reference body, which in particular has a circular central opening and a substantially equal diameter and/or a substantially equal height of the wall sections of the ring pessary delimiting the central opening. The diameter, circumference and/or height of the ring pessary as a reference body can preferably correspond to the diameter, circumference and/or height of the anterior and/or posterior wall section of the pessary according to the invention.

The term "rigidity" within the meaning of the invention relates in particular to the resistance of the pessary to an external force acting on a wall section, in particular on opposite wall sections, further in particular on both side wall sections of the base body in the direction towards the center of the vaginal pessary or when (laterally) compressing the vaginal pessary in the region of the wall sections. Further in particular, the term "rigidity" within the meaning of the invention relates to the resistance of the pessary to the application of a compressive force to the wall portions in the proximal direction below the at least one pocket-like deepening.

In comparative calculations, stiffnesses against deformation were determined when applying tensile and compressive forces to side wall sections of a pessary according to the invention below pocket-shaped deepenings and a ring pessary as a reference object. In particular, comparative calculations were carried out for a pessary according to the invention, the geometry of which is similar to a ring pessary with a non-circular cross-section, whereby the side wall sections have a greater height compared to the posterior and anterior wall sections and are tab-like and/or taper distally. The posterior and anterior wall sections have an essentially circular cross-section. In the central area of the respective side wall section, the side wall section reaches a maximum height and a pocket-like deepening is provided in each case. The diameter, circumference and/or height of the ring pessary as a reference body corresponds to the diameter, circumference and height of the anterior and/or posterior wall section of the pessary according to the invention. During the calculations, it was determined that the stiffness of the pessary according to the invention is between 30% and 100% of the stiffness of the ring pessary as a reference object.

Alternatively or additionally, it is provided that the deepening is formed by a wall section of the base body which has a higher elasticity and/or a lower wall thickness and/or a lower hardness compared to wall sections of the base body adjacent to the deepening. In particular, a reduced wall thickness enables improved deformability and/or increased flexibility of the pessary in the area of the deepening in order to correspondingly strengthen and/or generate the suction effect.

Preferably, the deepening is formed by a thin-walled wall section of the base body, which has a material thickness or wall thickness reduced by at least 40%, preferably at least 60%, particularly preferably at least 80%, very particularly preferably at least 90%, compared to an adjacent wall section of the base body without a deepening.

Alternatively or additionally, the thin-walled wall section, in particular in the center of the recess, has a thickness in the range of 0.1 mm to 4 mm, preferably 0.5 to 3 mm, particularly preferably 0.5 to 2 mm.

Alternatively or additionally, the non-deepened wall section of the base body adjacent to the deepening has a thickness in the range from 3 to 12 mm, preferably in the range from 5 to 10 mm, particularly preferably in the range from 6 to 8 mm.

In principle, the base body or vaginal pessary can be manufactured using different manufacturing or production processes, for example vacuum molding, hand molding, forming or injection molding. It is particularly preferred that the shaping to form the pocket-like deepening is always carried out using an appropriate tool, regardless of the selected production process.

In principle, all plastics or silicones approved for medical applications, in particular casting compounds, liquid or solid silicones, can be used to manufacture the base body.

The base body is particularly preferably made and/or formed from a silicone plastic.

Alternatively or additionally, the base body is made of a plastic material with proven biocompatibility in accordance with DIN EN ISO 10993.

The hardness of the material used can vary between a Shore hardness of 30 to 80 Shore A, depending on the shape, from solid to delicate.

Preferably, the Shore hardness is selected in such a way that the rigidity of the vaginal pessary with an integrally formed pocket-like deepening is between 30 and 100% of the rigidity of a vaginal pessary without a pocket-like deepening and/or a ring pessary with approximately the same circumference and/or approximately the same diameter.

Preferably, at least one deepening, in particular of the same shape or size, is provided in each side wall section, with the deepenings preferably being arranged opposite each other. This enables improved adhesion of the vaginal pessary on both sides.

However, it may also be provided that additionally or alternatively at least one deepening is provided or formed in the posterior wall section. It is not excluded that additionally or alternatively at least one deepening is formed in the anterior wall section.

Preferably, the volume of the cavity is between 1 and 10 milliliters (ml), preferably between 2 and 4 ml.

Alternatively or additionally, the opening area of the deepening on the outside of the base body is between 1 and 8 $cm^2$, preferably between 2 and 3 $cm^2$.

In particular, in relation to a side view of the vaginal pessary or to an outer contour line of the vaginal pessary in the side view, the proportion of the opening area of the deepening to the total contour area of the vaginal pessary can be between 20% and 70%, preferably between 20% and 30%.

The deepening is particularly preferably curved inwards or dome-shaped and pressed in towards the center of the central opening of the base body of the pessary.

The contour line of the deepening is preferably elongated, ovoid, preferably elliptical, with reference to a side view of the wall section of the pessary having the deepening. However, it is also possible for the inner contour to be circular.

Further advantages, special features and/or characteristics are shown in the following description of the drawings. It is understood that the features of the various embodiments of the invention described above and shown below can be combined with each other as required, even if this is not expressly mentioned in detail. The invention is not limited to the embodiments shown. The chosen paragraph formatting does not prevent a combination of features from different paragraphs.

The invention is explained in more detail below in conjunction with the drawing using preferred embodiments. The figures first show the features listed under the numbers, which are then explained in more detail.

BRIEF DESCRIPTION OF THE DRAWINGS

FIG. 17 is a table showing tensile measurements on the porcine vagina model.

DETAILED DESCRIPTION

Figure 1:
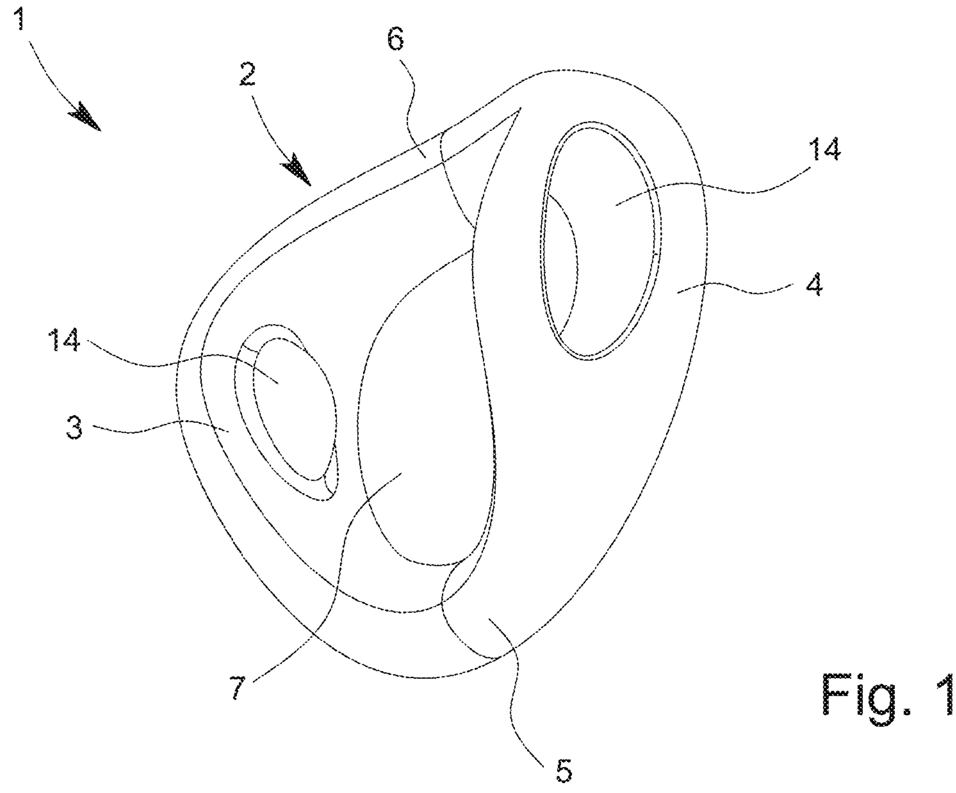
FIG. 1 is a perspective view of a vaginal pessary of the invention according to a first embodiment.

FIGS. 1 to 5 show a vaginal pessary 1 according to a first embodiment, which is used as a vaginally insertable support structure for prolapse complaints, for example after childbirth and/or as a recovery or fixation aid.

The vaginal pessary 1 has a circumferentially closed base body 2, which is designed or dimensioned for vaginal insertion for the purpose of support in the introitus area (entrance to the vagina) and/or with a lowered uterus.

The base body 2 has two side wall sections 3, 4, a front or anterior wall section 5 and a rear, posterior wall section 6.

In an inserted state of the base body 2, the anterior wall section 5 is in an orientation or alignment directed towards the front of the body, whereas the rear or posterior wall section 6 is in an orientation or alignment directed towards the rear or back of the body.

The lateral or side wall sections 3, 4 located between the anterior wall section 5 and the posterior wall section 6 are accordingly assigned to opposite sides of the patient's body, i.e. the left or right side of the body. In the inserted state, the base body 2 rests directly or circumferentially on the outside against adjacent tissue sections, in particular in such a way that body areas or organs to be supported, such as the uterus, are held or supported in the opposite direction to the direction of gravity by means of the vaginal pessary 1 or the base body 2.

The base body 2 has a central opening 7 which, in a cross-sectional view transverse to the height of the base body 2, is bounded by a closed, inner contour line 8 of the wall sections 3, 4, 5 and 6. The cross-sectional view transverse to the height of the base body 2 is ultimately to be understood as parallel to the plan view of the base body 2 shown in FIG. 2.

Figure 2:
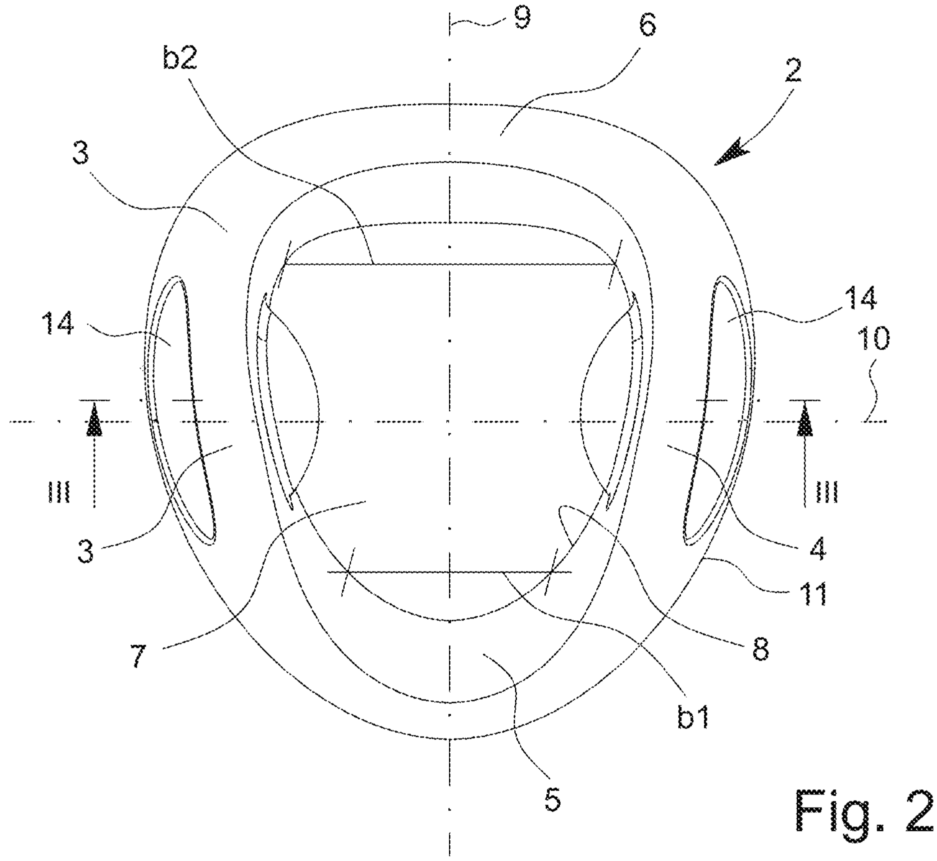
FIG. 2 is a schematic top view of the vaginal pessary according to FIG. 1.

The inner contour line 8 defines an essentially oval-shaped opening 7 that deviates from the circular shape, as shown in FIG. 2.

The deviation from the circular shape can ultimately be of any shape, whereby circular contour sections can be provided along the inner contour line 8. However, at least one section is then provided along the inner contour line 8 in such a way that an opening 7 deviating from the circular shape is created, in particular in relation to the top view of the base body 2 shown in FIG. 2. The opening 7, which deviates from the circular shape, can be asymmetrical and ultimately take the form of any oval in order to form an inner contour line 8 that deviates from the circular shape.

In the illustrated and preferred embodiment example, the inner contour line 8 is symmetrical to a central longitudinal axis 9 of the base body 2 and has, in particular, an essentially egg shape.

It is shown and preferred that the contour line 8 has a pointed or short end on the side of the anterior wall section 5 and a long or blunt end on the side of the posterior wall section 6. Accordingly, the opening 7 in the region of the anterior wall section 5 has a smaller width, i.e. opening width, than in the region of the posterior wall section 6.

The different width of the opening 7 is to be understood in particular in relation to a central transverse axis 10 of the opening 7 and/or the base body 2 running transversely to the central longitudinal axis 9.

With reference to the same distance to the central transverse axis 10, the opening 7 in the area of the anterior wall section 5 has a reduced opening width b1 than in the area of the posterior wall section 6 with a larger width b2.

Starting from the central transverse axis 10, the width of the opening 7 decreases towards the anterior wall section 5, whereas the width initially increases starting from the central transverse axis 10 towards the posterior wall section 6 and then decreases significantly immediately before the posterior wall section 6.

The base body 2 has an outer contour line 11 opposite the inner contour line 8, with the outer contour line 11 following the course of the inner contour line 8 at least substantially and/or in sections. In other words, the base body 2 is at least substantially ring-shaped with contour lines 8, 11 that are adapted to one another, in particular parallel to one another at least in sections.

The inner contour line 8 and/or the outer contour line 11 is or are at least substantially mirror-symmetrical to the central longitudinal axis 9 and/or the central transverse axis 10 of the base body 2. In the case of mirror symmetry in relation to the central longitudinal axis 9, a preferably egg-shaped opening 7 is provided. If the mirror symmetry is present in relation to both central axes 9, 10, the opening 7 or the contour lines 8, 11 are preferably elliptical in shape. The shape to be selected is therefore varied and can be individually adapted to the intended application.

The opposing side wall sections 3, 4 are preferably curved in a substantially uniform convex manner, in particular wherein the inner contour line 8 and the outer contour line 11 are each curved in a uniform convex manner in the region of the side wall sections 3, 4.

However, it is also possible for the inner contour line 8 and/or the outer contour line 11 to be straight in the area of the side wall sections 3, 4.

Figure 3:
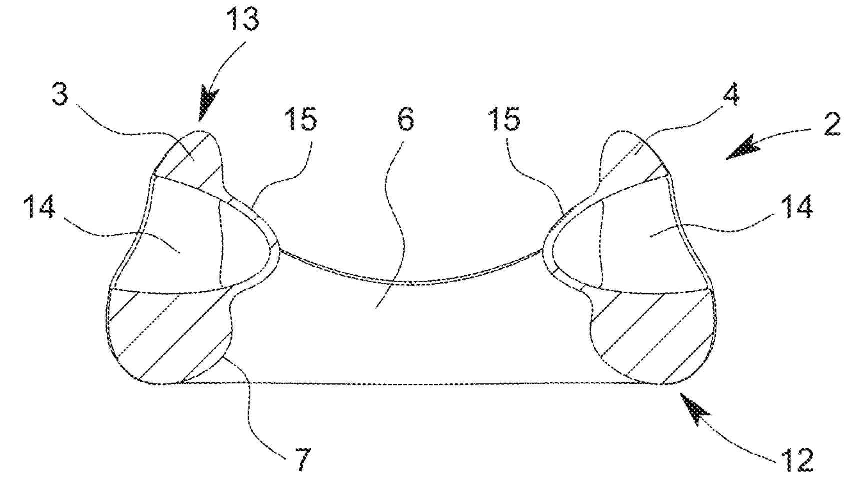
FIG. 3 is a cross-sectional view of the vaginal pessary from FIG. 2 along section line III-III.

As can be seen from FIG. 3, the thickness of the wall sections, preferably the side wall sections 3, 4, decreases starting from a proximal outer side 12 of the base body 2 in the direction towards a distal outer side 13 of the base body 2. In the inserted state, the proximal outer side 12 is directed towards the center of the body, whereas the distal outer side 13 is directed away from the center of the body. The decreasing thickness of the base body 2 towards the distal outer side 13 allows further improvement or adaptation of the base body 2 in the area of use, particularly with regard to close contact between the base body 2 and the adjacent tissue. This ensures secure support of the tissue sections on the vaginal pessary 1.

As illustrated in FIG. 1, the base body 2 has a height that preferably changes continuously in the circumferential direction. With a constantly changing height, there is preferably no abrupt transition or no abrupt change in height in the circumferential direction of the base body 2.

In the illustrated and preferred embodiment example, the side wall sections 3, 4 are raised relative to the anterior wall section 5 and/or the posterior wall section 6.

Figure 4:
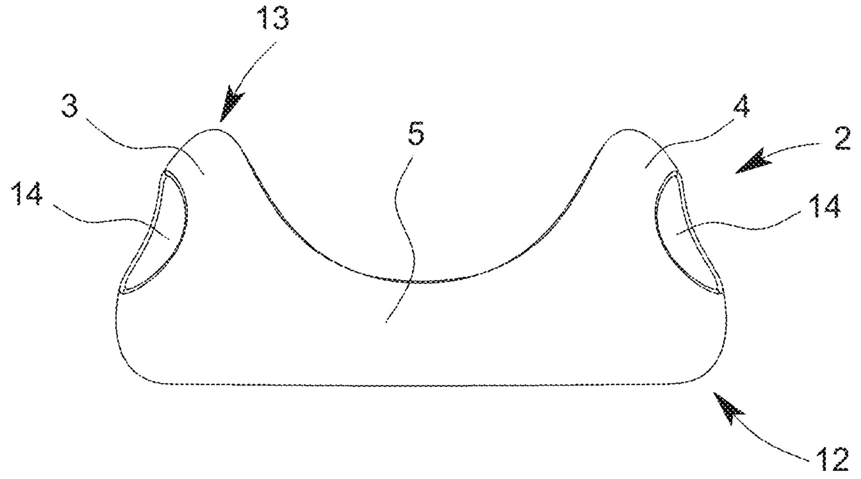
FIG. 4 is a front view of the vaginal pessary of the invention according to the first embodiment.
Figure 5:
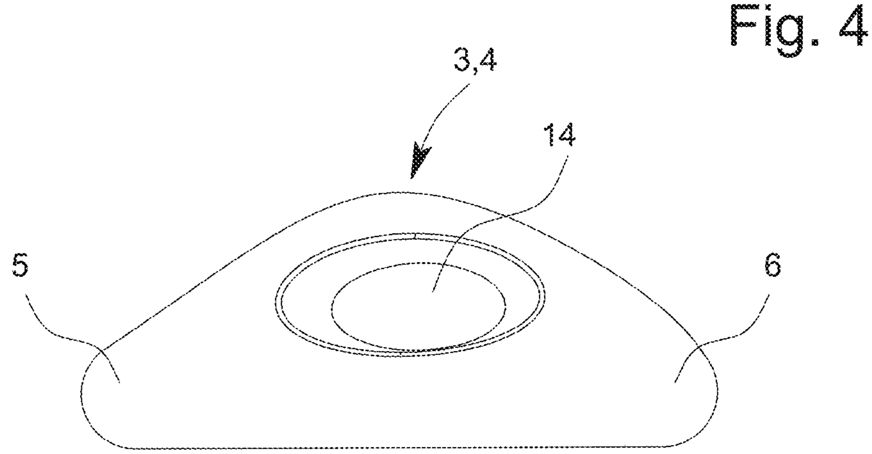
FIG. 5 is a side view of the vaginal of the invention according to the first embodiment.

As illustrated in FIGS. 4 and 5, the side wall sections 3, 4 have the same maximum height. In particular, the side wall sections 3, 4 form protruding flaps with a curved upper side in relation to the posterior wall section 5 and the anterior wall section 6. This makes it easier to insert the base body 2 into the vagina. However, the side wall sections 3, 4 can also have different heights.

The posterior wall section 5 and the anterior wall section 6 preferably have the same, in particular minimal, height compared to the side wall sections 3, 4. However, a different height between the anterior wall section 5 and the posterior wall section 6 is also possible.

According to a further special feature of the present invention, which can also be realized independently, the base body 2 has a pocket-shaped deepening 14 opened on the outside of the base body 2 in order to form a better attachment for adjacent tissue in the insertion state of the vaginal pessary 1.

In the illustrated and preferred embodiment example, the side walls 3, 4 each have a deepening 14, which is designed to project radially inwards and/or radially into the opening 7, as shown in FIG. 2.

The aspect of the pocket-shaped deepening 14 is particularly preferred in conjunction with an egg-shaped inner contour line 8. In this way, an improved adaptability can be achieved in combination with a secure connection of the vaginal pessary 1.

FIG. 3 illustrates that the deepenings 14 on the inside of the base body 2, namely on the side of the central opening 7, are closed. In this case, the deepenings 14 on the inside of the base body 2 are bounded by a further or thin-walled wall section 15, which has a reduced material thickness and/or elasticity compared to the wall sections, preferably side wall sections 3, 4 of the base body 2, adjacent to the deepenings 14. Particularly preferably, the deepenings 14 are turned out inwards at the wall sections 15.

Preferably, the thin-walled wall section 15 has a material thickness that is reduced by at least 40%, preferably at least 60%, particularly preferably at least 80%, very particularly preferably at least 90%, compared to the wall section adjacent to the deepening 14, preferably an associated side wall section 3, 4.

The thin-walled wall sections 15 make it possible to reduce the suction volume within the deepenings 14 in the run-up to the operational state in order to achieve a suction effect on this basis when the wall sections 15 align themselves radially inwards again in the operational state due to their elasticity and a negative pressure builds up within the deepenings 14 as a result.

The thin-walled wall sections 15 preferably have a thickness in the range from 0.1 mm to 4 mm, preferably from 0.5 mm to 3 mm, in particular from 0.5 mm to 2 mm, particularly preferably from 0.5 mm to 1 mm, especially in the center.

The base body 2 can be manufactured using conventional production methods, for example by injection molding, casting and/or pressing with an elastomeric plastic and/or silicone.

Figure 6:
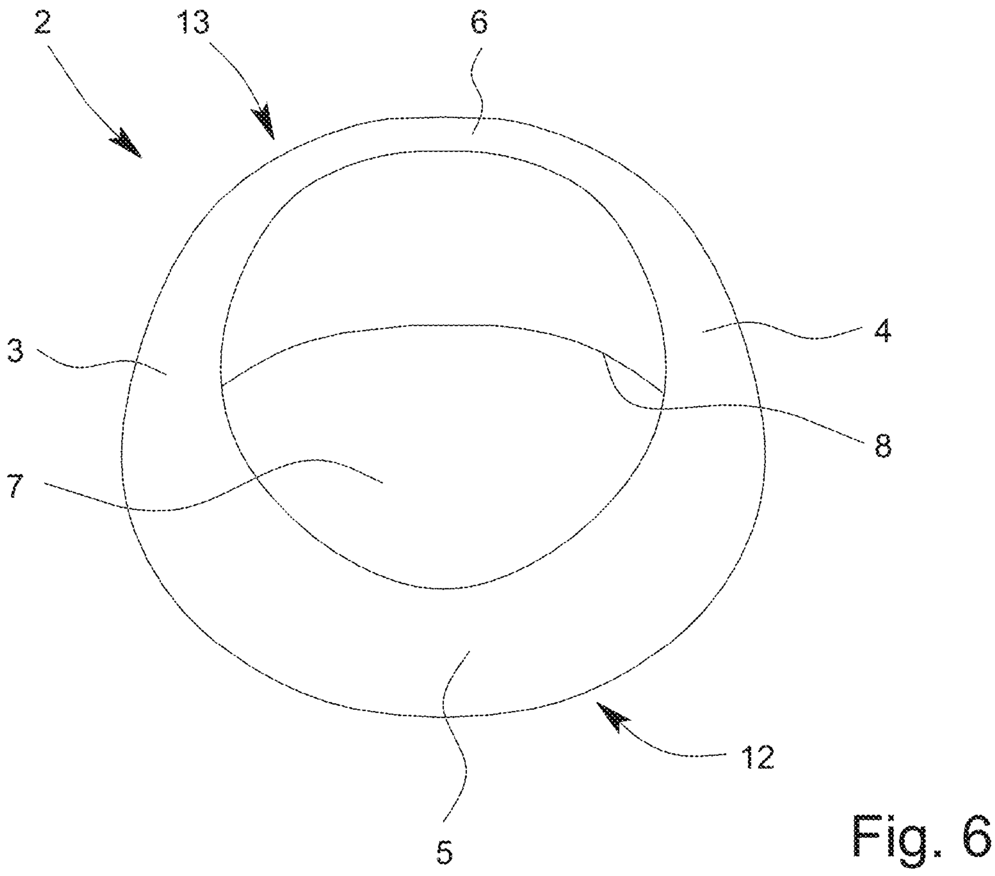
FIG. 6 is a perspective front view of the vaginal pessary of the invention according to a second embodiment.

In the embodiment shown in FIG. 6, the base body 2 has a height that changes continuously in the circumferential direction, with a minimum height being reached at the anterior wall section 5 and a maximum height being reached at the posterior wall section 6. The constantly changing height is preferably to be understood in relation to the distal outer side 13 of the base body 2, with the proximal outer side 12 preferably having a constant height and/or providing for small height changes in the circumferential direction.

The distal outer side 13 or upper side of the base body 2 is preferably beveled.

It is understood that the features shown above with regard to the first embodiment, insofar as they do not contradict the second embodiment of the vaginal pessary 1 according to FIG. 6, also apply correspondingly to the vaginal pessary 1 according to the second embodiment.

Figure 7:
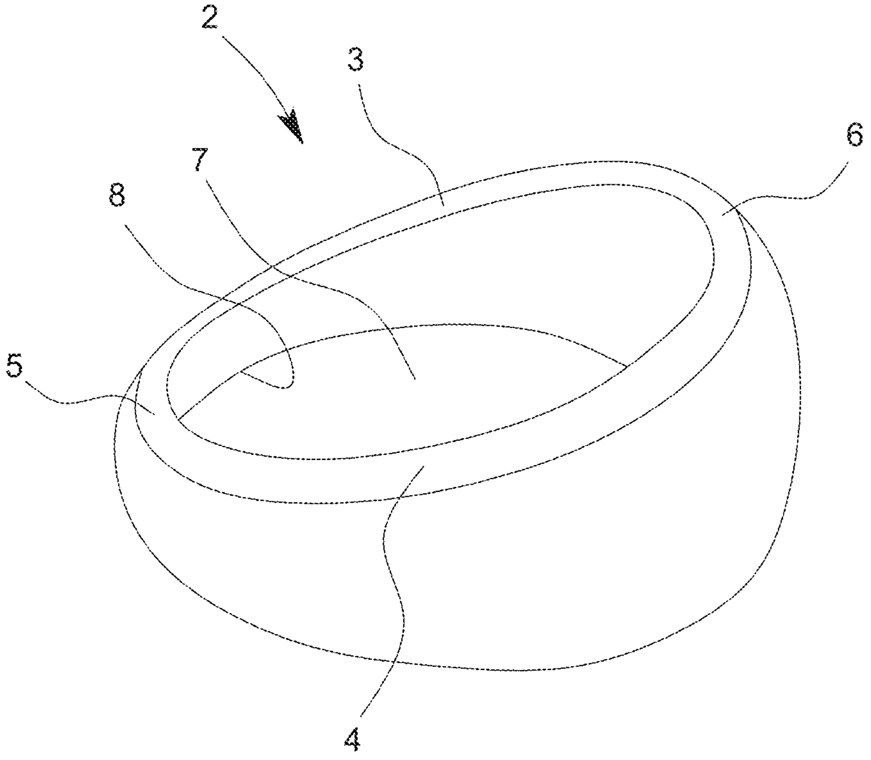
FIG. 7 is a perspective side view of the vaginal pessary according to the invention from FIG. 6.

Accordingly, with reference to FIG. 7, the vaginal pessary 1 according to the second embodiment has a central opening 7 whose inner contour line 8 of the wall sections 3, 4, 5 and 6 has an essentially oval shape that deviates from the circular shape.

Figure 8:
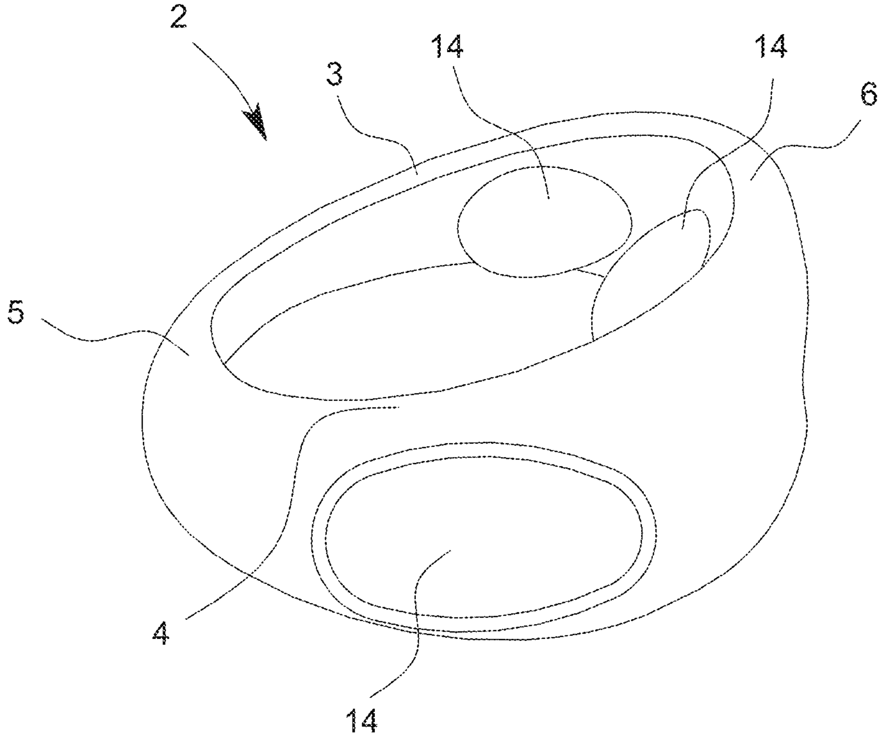
FIG. 8 is a perspective side view of the vaginal pessary of the invention according to a third embodiment.
Figure 9:
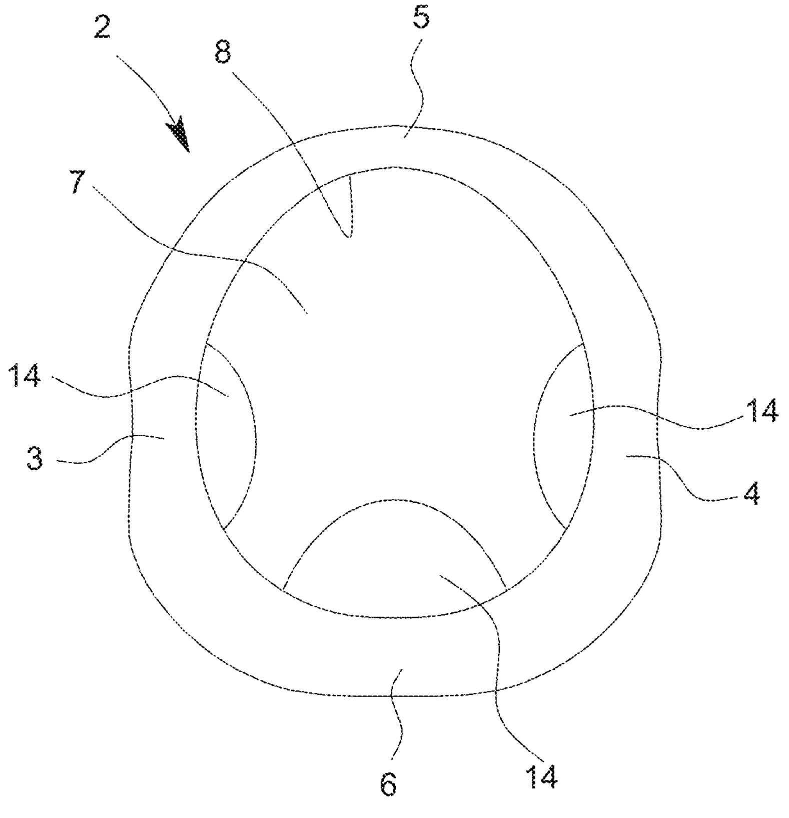
FIG. 9 is a top view of the vaginal pessary from FIG. 8.

The third embodiment of the vaginal pessary 1 according to the invention shown in FIGS. 8 and 9 essentially corresponds to the second embodiment, with the base body 2 having more than two deepenings 14, three in the example shown. One deepening 14 is located on each of the opposing side wall sections 3, 4. In addition, a further deepening 14 is also arranged on the posterior wall section 6.

However, it is understood that, as described in connection with the second embodiment, only two deepenings 14 can be provided on the opposing side wall sections 3, 4.

As can be seen in FIG. 9, the deepenings 14 can be of different sizes and/or have different receiving volumes. Particularly preferably, the deepenings 14 assigned to the side walls 3, 4 are of the same size, whereas the deepening 14 assigned to the posterior wall section 6 has a larger receiving volume in comparison.

Figure 10:
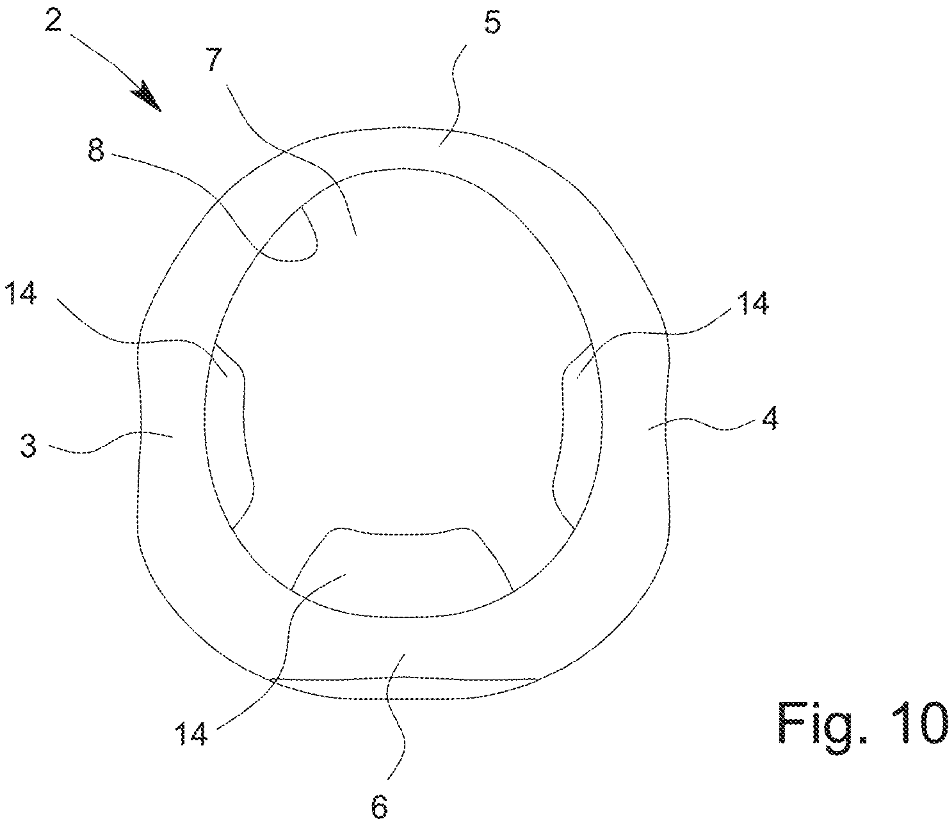
FIG. 10 is a top view of the vaginal pessary of the invention according to a fourth embodiment.
Figure 11:
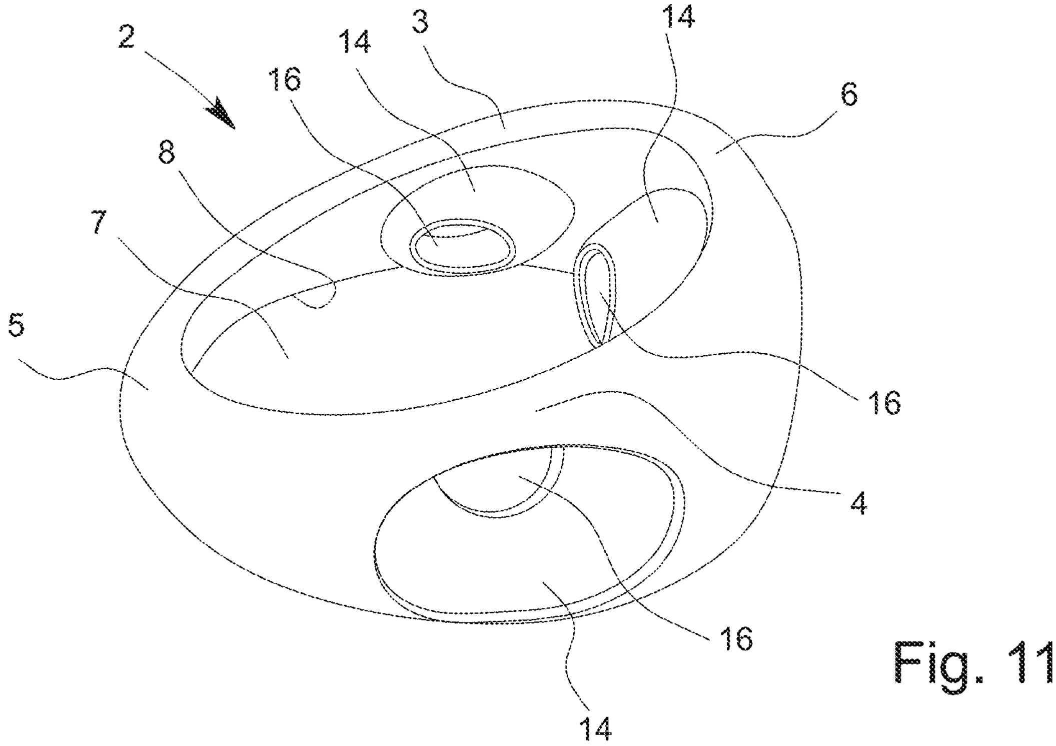
FIG. 11 is a perspective side view of the vaginal pessary from FIG. 10.

In the fourth embodiment shown in FIGS. 10 and 11, it is provided that at least one deepening 14 is open radially or on the inside.

Accordingly, at least one, preferably each, deepening 14 has a breakthrough 16, as illustrated in FIG. 11.

Despite the breakthroughs 16, a sufficient suction effect is ensured when the vaginal pessary 1 is inserted. At the same time, this results in further increased elasticity, as the thin-walled wall section 15 of the deepening 14 is further weakened and/or made more elastic by the breakthrough 16. At the same time, the breakthrough 16 allows fluid to drain out of the base body 2.

Figure 12:
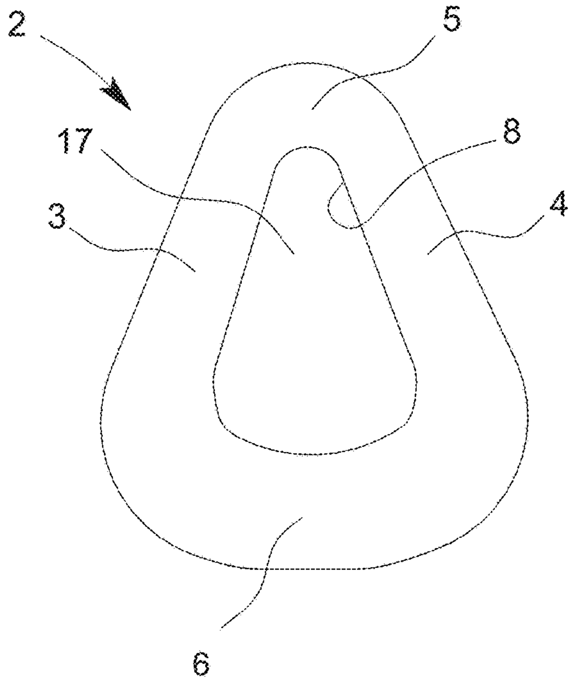
FIG. 12 is a top view of the vaginal pessary according to a fifth embodiment.

In the following, FIGS. 12 to 14, embodiments are described in which the inner contour line 8 is delimited by a substantially trapezoidal opening 17.

The contour line 8 is essentially straight in the area of the opposing side wall sections 3, 4. However, it is also possible for the contour line 8 to be preferably slightly convex in the area of the opposing side wall sections 3, 4, whereby a trapezoidal opening 17 is also present.

The contour line 8 is correspondingly convexly curved in the area of the anterior wall section 5 and the posterior wall section 6. However, it is also possible to form the anterior and/or posterior wall section 5, 6 in a straight line, in particular to form an exactly trapezoidal inner contour line 8 or central opening 17.

Figure 13:
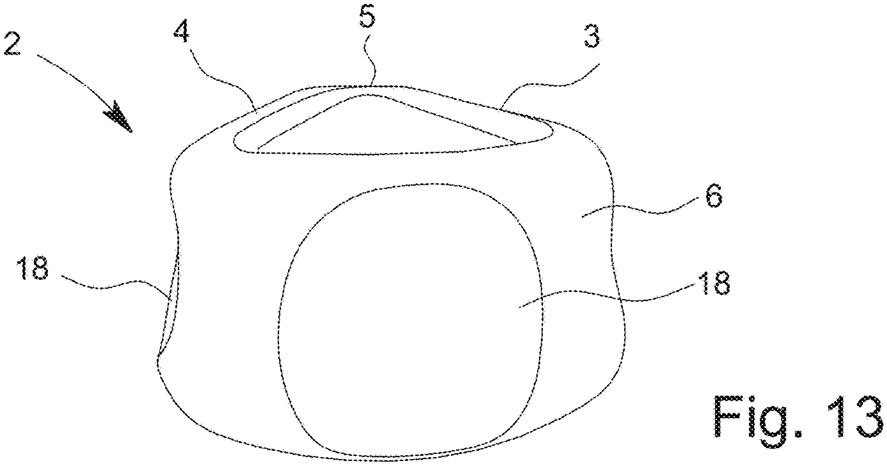
FIG. 13 is a perspective rear view of the vaginal pessary according to a sixth embodiment.

In the sixth embodiment shown in FIG. 13, the base body 2 with the trapezoidal inner opening 17 or inner contour line 8 has at least one notch 18. In the illustrated and preferred embodiment example, this notch 18 is formed on the posterior wall section 6.

Figure 14:
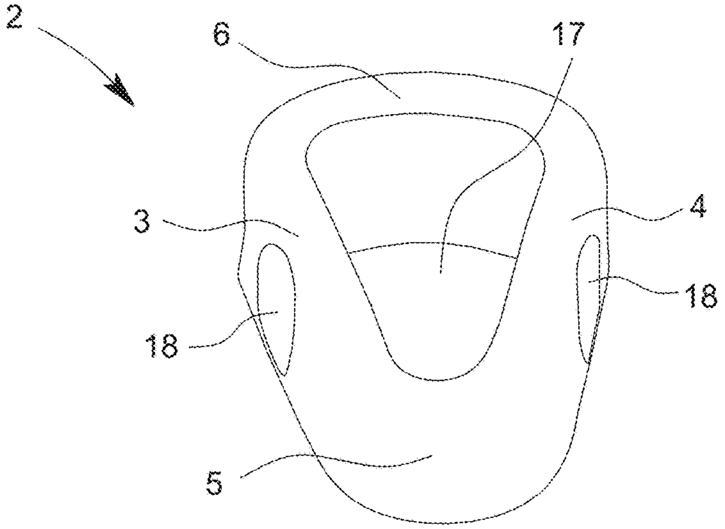
FIG. 14 is a further rear view of the vaginal pessary from FIG. 13.

In addition, in this embodiment, as shown in FIG. 14, a further notch 18 is also provided on each of the side wall sections 3, 4.

Figure 15:
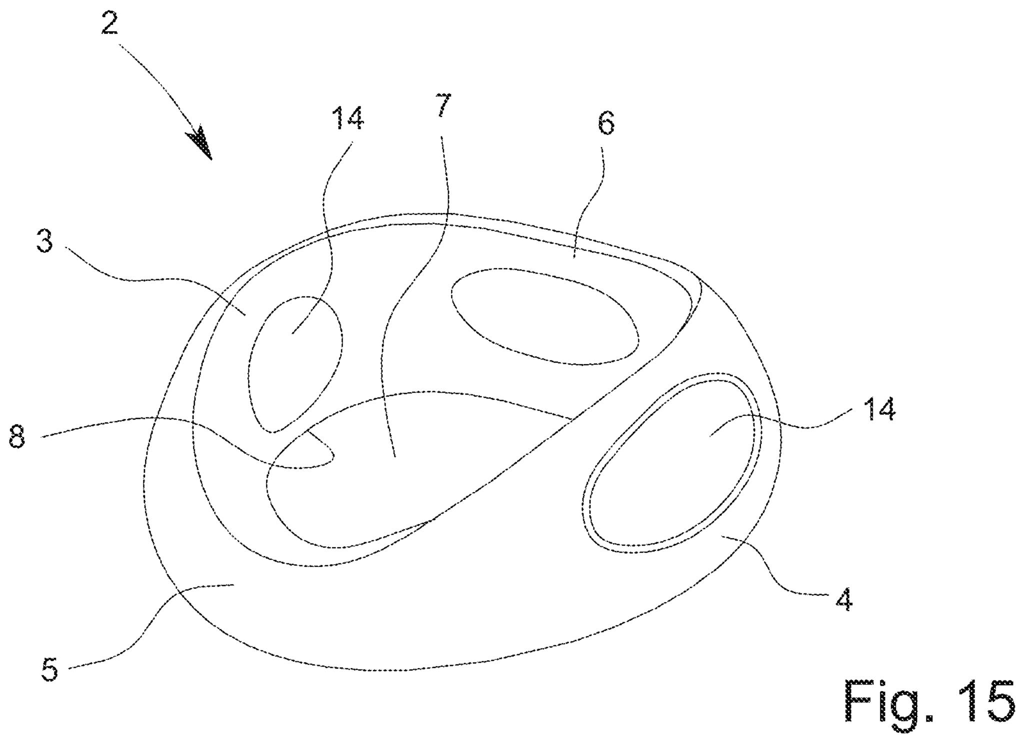
FIG. 15 is a perspective view of the vaginal pessary of the invention according to a sixth embodiment.
Figure 16:
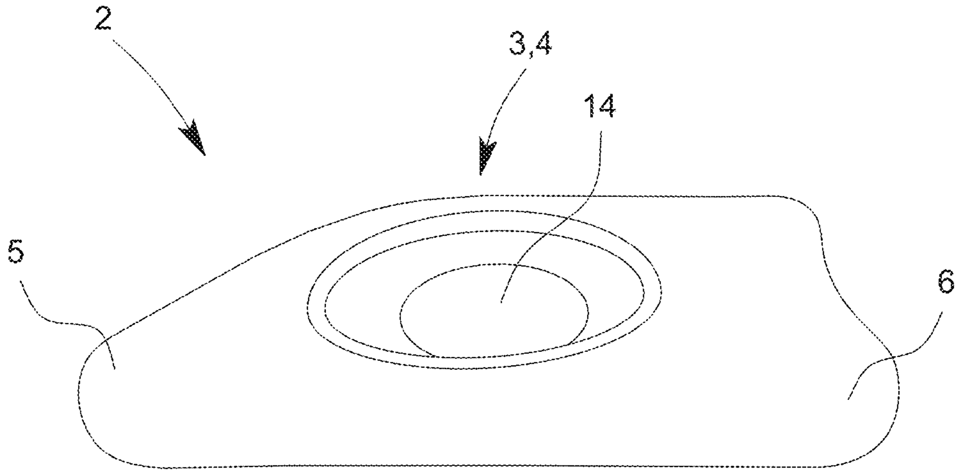
FIG. 16 is a side view of the vaginal pessary from FIG. 15.

In the seventh embodiment shown in FIGS. 15 and 16, the posterior wall section 6 and the side wall sections 3, 4 have the same maximum height. In particular, the posterior wall section 6 together with the side wall sections 3, 4 form a plateau area.

The minimum height of the base body 2 is present at the anterior wall section 5, in particular whereby, starting from the anterior wall section 5, the height of the base body 2 increases on both sides in the direction of the side wall sections 3, 4 and finally reaches the maximum height at the side wall sections 3, 4.

In the embodiment example shown, the side wall sections 3, 4 and the posterior wall section 6 each have a closed recess 14.

The following features can preferably be realized equally in relation to all embodiments:

The base body 2 has a width in the range from 50 to 80 mm, preferably from 55 to 65 mm, most preferably around 60 mm.

The base body 2 has a length in the range of 55 to 90 mm, preferably in the range of 60 to 75 mm.

The base body 2 has a maximum height in the range of 15 to 45 mm, preferably in the range of 25 to 35 mm.

The base body 2 has a minimum height in the range of 5 to 15 mm, preferably in the range of 8 to 12 mm.

The maximum width, i.e. opening width, of the opening 7 and/or 17 is in the range of 30 to 50 mm, preferably in the range of 35 to 40 mm.

The base body 2 has a front, preferably bead-like, reinforcement, in particular where the reinforcement is formed on the anterior wall section 5.

The deepening 14 or the receiving volume of the deepening 14 is semi-elliptical and/or dome-shaped. The receiving volume can also be hemispherical and/or semi-elliptical.

Individual aspects and features of the present invention, in particular of the various embodiments, may be realizable and advantageous individually and in various combinations.

Validation: Production of Custom-Made Products for Individual Patients at the Request of Doctors Under Confidentiality Provisions, Also as Part of a ZIM Project and Summary of the Findings:

General Impression:

1) The application of models with indentations on the side walls is particularly suitable for younger women with complaints after childbirth, as the models have a high adhesive force and also allow the fluorine to drain away.
2) The application with additional indentation on the posterior wall is more suitable for older patients after prolapse surgery for additional support,
3) The prolapse symptoms were significantly improved in both groups
4) All the models used were suitable for "self-management", i.e. they could be easily changed by the patient herself.
5) During a specialist examination (Prof. Dietz), transperineal ultrasound also showed contractions of the pelvic floor muscles in high-risk patients with previous damage and a reduction in the hiatus opening.

LIST OF REFERENCE SIGNS

1 Vaginal pessary
2 Base body
3 Side wall section
4 Side wall section
5 anterior wall section
6 posterior wall section
7 Central opening
8 Inner contour line
9 Central longitudinal axis
10 Central transverse axis
11 Outer contour line
12 proximal outer side
13 distal outer side
14 Deepening
15 thin-walled wall section
16 Breakthrough
17 trapezoidal opening
18 Notch
b1 Width
b2 Width

LITERATURE

1) Harvey M A, Lemieux M C, Robert M, Schulz J A. Guideline No. 411: Vaginal Pessary Use. J Obstet Gynaecol Can. 2021; 43 (2): 255-66 el. doi: 10.1016/j.jogc.2020.11.013.
2) Tunn R, Albrich S, Beilecke K, Kociszewski J, Lindig-Knopke C, Reisenauer C, et al. Interdisciplinary S2k Guideline: Sonography in Urogynecology: Short Version—AWMF Registry Number: 015/055. obstetrics gynecology. 2014; 74(12):1093-8. doi: 10.1055/s-0034-1383044.
3) Santé HAd. Prolapsus génital de la femme-des solutions pour le traiter. 2022. doi: https://www.has-sante.fr/upload/docs/application/pdf/2022-04/reco443_fiche_patient_principale_prolapsus_cd_2022_04_28_v0.pdf. Accessed: 21.12.2022.
4) National Institute for Health and Care Excellence. NICE Guidance—Urinary incontinence and pelvic organ prolapse in women: management: (c) NICE (2019) Urinary incontinence and pelvic organ prolapse in women: management. BJU Int. 2019; 123(5):777-803. doi: 10.1111/bju.14763.
5) Lone F, Thakar R, Sultan A H. One-year prospective comparison of vaginal pessaries and surgery for pelvic organ prolapse using the validated ICIQ-VS and ICIQ-UI (SF) questionnaires. Int Urogynecol J. 2015; 26(9):1305-12. doi: 10.1007/s00192-015-2686-9.
6) Dietz H P, Walsh C, Subramaniam N, Friedman T. Levator avulsion and vaginal parity: do subsequent vaginal births matter? Int Urogynecol J. 2020; 31(11):2311-5. doi: 10.1007/s00192-020-04330-4.
7) Hilde G, Stær-Jensen J, —Siafarikas F, Ellström M, Bø K: Postpartum pelvic floor muscle training, levator ani avulsion and levator hiatus area: a randomized trial. Int Urogynecol J 2023; 34:413-23. doi: 10.1007/s00192-022-05406-z

The invention claimed is:

1. A vaginal pessary comprising:

a circumferentially closed base body, wherein the base body has two side wall sections, a front, anterior wall section and a rear, posterior wall section, and wherein a central opening of the base body in a cross-sectional view transversely to a height of the base body is delimited by a closed, inner contour line of the wall sections;

wherein the central opening delimited by the inner contour line of the wall sections has an egg-shape which deviates from a circular shape, the central opening having rounded edges with a pointed end on the anterior wall section and a blunt end on the posterior wall section and/or the inner contour line having an elliptical shape;

wherein the two side wall sections are flap shaped and are raised relative to the anterior wall section and the posterior wall section; and wherein the two side wall sections each have a pocket-shaped deepening opened on an outside of the base body, which deepenings are configured to induce a suction or adhesion zone for adjacent vaginal tissue during and after insertion of the vaginal pessary.

2. The vaginal pessary according to claim 1, wherein at least one further deepening is provided in the rear, posterior wall section, wherein a receiving volume of the further deepening is between 1 and 10 milliliters.

3. The vaginal pessary according to claim 2, wherein the receiving volume of the further deepening is between 2 and 4 milliliters.

4. The vaginal pessary according to claim 1, wherein at least one further deepening is provided in the rear, posterior wall section, wherein an opening surface of the further deepening is between 1 and 8 $cm^2$.

5. The vaginal pessary according to claim 4, wherein the opening surface of the further deepening is between 2 and 3 $cm^2$.

6. The vaginal pessary according to claim 1, wherein the front, anterior wall section and/or the rear, posterior wall section on a side of the central opening is convexly curved in the cross-sectional view, and wherein the front, anterior wall section and/or the rear, posterior wall section on the side of the central opening is differently convexly curved in the cross-sectional view.

7. The vaginal pessary according to claim 1, wherein the inner contour line of the wall sections is mirror-symmetrical to a central longitudinal axis and/or to a central transverse axis.

8. The vaginal pessary according to claim 1, wherein the wall sections of the base body merge into one another all the way around the base body.

9. The vaginal pessary according to claim 1, wherein the height of the base body changes continuously in a circumferential direction around the base body, a minimum height of the base body being reached at the anterior wall section and/or a maximum height of the base body being reached at the posterior wall section.

10. The vaginal pessary according to claim 1, wherein each deepening is formed on an inner side of a respective one of the two side wall sections on a side of the central opening.

11. The vaginal pessary according to claim 1, wherein each deepening is closed or open on an inner side of the base body, on a side of the central opening.

12. The vaginal pessary according to claim 1, wherein each deepening on an inner side of the base body is delimited by a respective thin-walled wall section which has a higher elasticity and/or lower wall thickness than respective side wall sections adjacent to each deepening of the base body.

13. The vaginal pessary according to claim 1, wherein the side wall sections are uniformly convexly curved on a side of the central opening.

14. The vaginal pessary according to claim 1, wherein the inner contour line has a continuously convex course along the central opening; and wherein the inner contour line is more curved and/or convexly bent in a region of the front, anterior wall section than in a region of the rear, posterior wall section.

15. The vaginal pessary according to claim 1, wherein the inner contour line has a continuously convex course along the central opening; and wherein a thickness of the side wall sections decreases starting from a proximal outer side of the base body in a direction of a distal outer side of the base body.

16. The vaginal pessary according to claim 1, wherein each deepening is directed radially inwards.

17. The vaginal pessary according to claim 1, wherein each deepening is delimited on an inner side of the base body by a respective thin-walled wall section which is turned out inwards with respect to the respective side wall sections of the base body adjoining each deepening.

18. The vaginal pessary according to claim 1, wherein the deepenings are arranged opposite one another in the two side wall sections.

19. The vaginal pessary according to claim 1, wherein at least one further deepening is provided in the rear, posterior wall section, wherein an opening surface of the further deepening has a convex and/or oval inner contour deviating from a circular shape in a side view.

* * * * *